(12) United States Patent
Wakabayashi et al.

(10) Patent No.: US 6,588,327 B2
(45) Date of Patent: Jul. 8, 2003

(54) PASTEURIZER

(75) Inventors: Norimitsu Wakabayashi, Tokyo (JP); Ryosuke Aika, Tokyo (JP); Yoshifumi Kawabata, Tokyo (JP); Fujio Komatsu, Tokyo (JP); Masami Kohama, Tokyo (JP)

(73) Assignees: Showa Tansan Co., Ltd., Tokyo (JP); Mayekawa Mfg. Co., Ltd., Tokyo (JP)

( * ) Notice: Subject to any disclaimer, the term of this patent is extended or adjusted under 35 U.S.C. 154(b) by 0 days.

(21) Appl. No.: 10/048,006

(22) PCT Filed: May 22, 2001

(86) PCT No.: PCT/JP01/04274

§ 371 (c)(1),
(2), (4) Date: Jun. 25, 2002

(87) PCT Pub. No.: WO01/89327

PCT Pub. Date: Nov. 29, 2001

(65) Prior Publication Data

US 2002/0170440 A1 Nov. 21, 2002

(30) Foreign Application Priority Data

May 25, 2000 (JP) ......................................... 2000-154557

(51) Int. Cl.[7] .............................. A23L 1/00; A23L 3/00; A23L 3/10; A23L 3/12; A61L 2/04
(52) U.S. Cl. ............................. 99/470; 99/367; 99/370; 99/467; 99/477; 99/483
(58) Field of Search .......................... 99/330, 359–371, 99/467, 468, 470, 477–479, 483, 352–355; 134/72, 131; 422/21, 22, 25–29, 38, 105, 292, 300, 307, 308, 304, 114; 426/510, 511, 520, 521, 523, 397; 165/66

(56) References Cited

U.S. PATENT DOCUMENTS

| 4,331,629 | A | * | 5/1982 | Huling ....................... 99/361 X |
| 4,441,406 | A | * | 4/1984 | Becker et al. ................. 99/275 |
| 4,490,401 | A | * | 12/1984 | Becker et al. ............... 426/407 |
| 4,693,902 | A | * | 9/1987 | Richmond et al. ........ 99/483 X |
| 4,727,800 | A | * | 3/1988 | Richmond et al. ............. 99/361 |
| 4,841,457 | A | * | 6/1989 | Clyne et al. ............. 426/521 X |
| 5,750,174 | A | * | 5/1998 | Lucassen ................... 99/470 X |
| 5,772,958 | A | * | 6/1998 | Nielsen ...................... 422/38 X |
| 6,019,033 | A | * | 2/2000 | Wilson et al. ................. 99/470 |

FOREIGN PATENT DOCUMENTS

| JP | 7265024 | 10/1995 |
| JP | 7265026 | 10/1995 |
| JP | 8280367 | 10/1996 |
| JP | 10225503 | 8/1998 |

* cited by examiner

Primary Examiner—Timothy F. Simone
(74) Attorney, Agent, or Firm—Crowell & Moring LLP (57) ABSTRACT

An energy and water saving pasteuriser capable of maintaining a stable temperature distribution pattern even when transfer work are interrupted during the operation, or a tunnel type refrigerator (10) allowing hot work such as bottles and cans filled with the products sterilized at a high temperature of generally 75° C. to allow temperature of generally 25° C., wherein plural cooling vessels (11a, 12a, 12b, 12c, 12d, 13a, 13b) are disposed in a row from the upstream side to the downstream side so as to form a first cooling region (11), an intermediate cooling region (12), and a final cooling region (13), an adsorption freezing machine (19) is installed between the first cooling region (11) and final cooling region (13), and a cooling tower (20) is installed in the intermediate cooling region (12).

8 Claims, 9 Drawing Sheets

PASTEURIZER

BACKGROUND OF THE INVENTION

1. Fields of the Invention

The present invention relates to a pasteurizer for hot sterilization or cold sterilization by cooling product liquid in work containers such as cans, bins and so forth or applying heat energy to product liquid that is filled in the work containers.

2. Description of the Related Art

Figure 3:
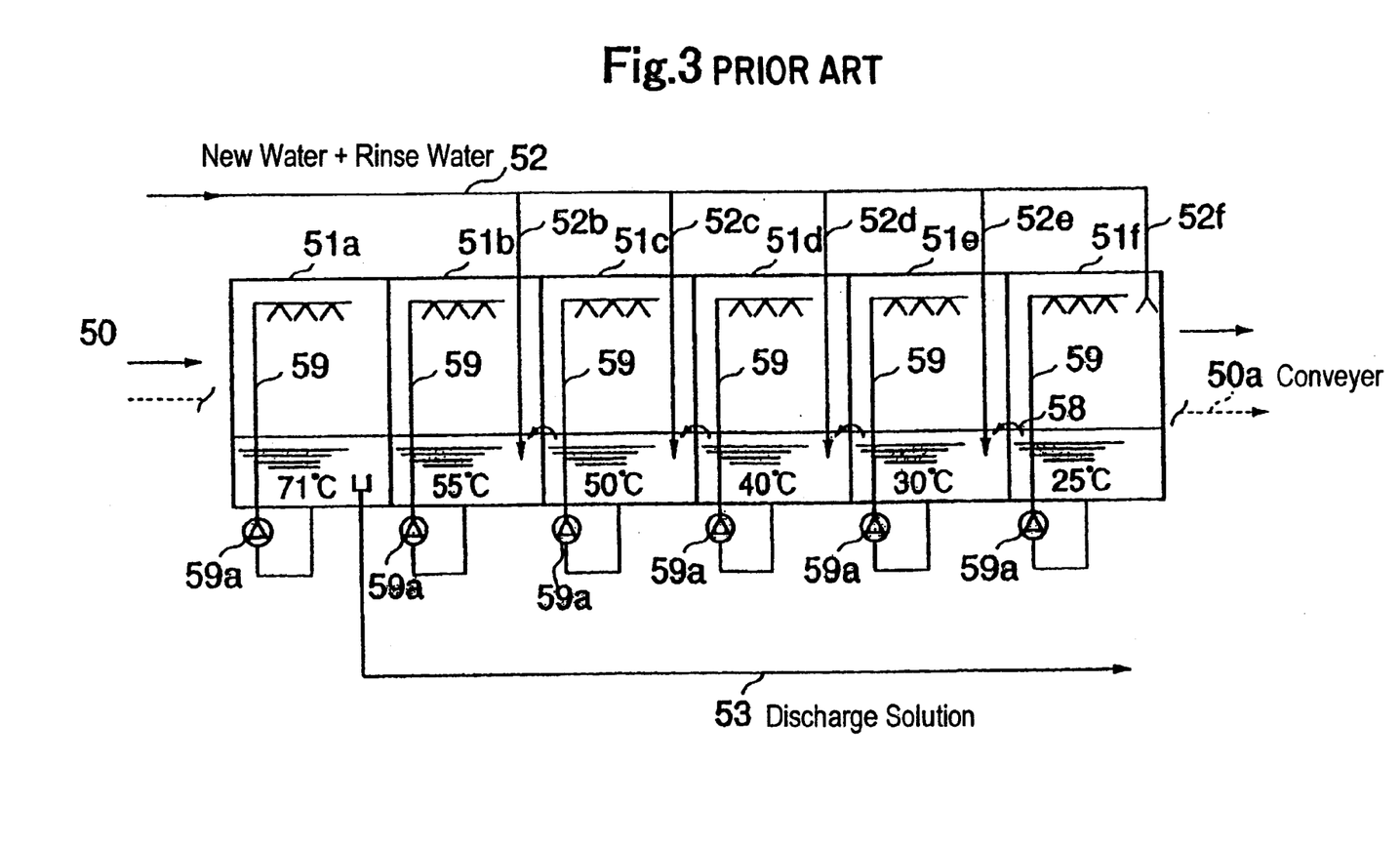
FIG. 3 is a schematic drawing of a pasteurizer for cooling of prior art.

A pasteurizer for cooling hot work containers such as cans, bins and so forth in which a sterilized product liquid is filled is known. As shown in FIG. 3 for example, a series of six cooling vessels 51a–51f are disposed from an upper stream toward a downstream to form a tunnel type continuous liquid jet heat exchanger. A solution 52 made by mixing a rinse water for cooling of approximately 15° C. with a pure water is provided to the cooling vessels 51b–51f through supplying pipes 52b–52f respectively.

In the cooling vessels 51a–51f, the cooling solution thus provided is sprayed to cool from the upper part of the cooling vessels on work 50 conveyed by a conveyer 50a by means of a circulating-spraying mechanism consisting of sprayers 59 and pumps for circulating-spraying 59a.

Thus, the work 50 in the condition of high temperature approximately 75° C., which has been filled with sterilized product under a high temperature, are cooled gradually while conveying through each cooling vessel finally to approximately 20° C. at the taking-out end of the downstream.

The cooling solution is made to flow in reverse to the upstream side from the cooling vessel 51f to the cooling vessel 51a of the upstream side by an overflow stream 58 so as to discharge the hot solution heated by heat exchange in the work-cooling process through a drainage disposed at the cooling vessel 51a as a discharge solution 53.

In the pasteurizer for cooling as shown in FIG. 3 and stated above, since the solution 52 supplied, for cooling is supplied evenly to each cooling vessel from the upstream to the downstream without having the difference of the supplying-solution temperature or the supplying-solution volume; so that a problem appeared concerning optimization of spraying temperature.

Figure 4A:
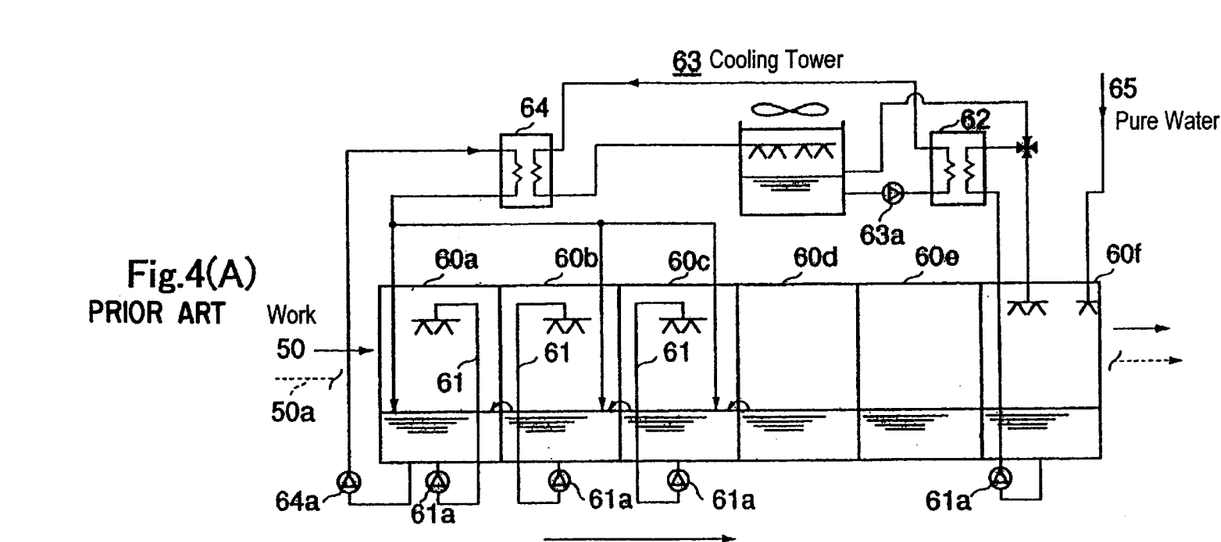
FIG. 4 is a schematic drawing of a pasteurizer for cooling of prior art as another example.

FIG. 4(A) indicates a schematic construction of another prior art of a pasteurizer for cooling.

Figure 4B:
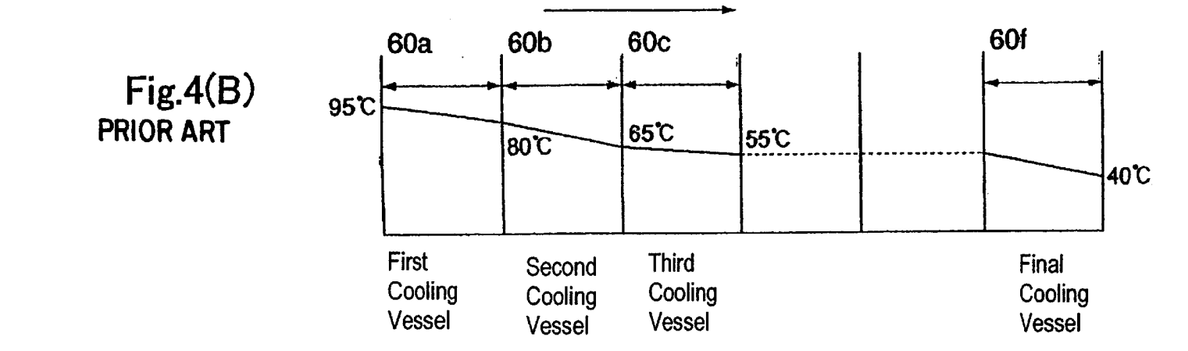

FIG. 4(B) illustrates the state of a temperature distribution of each cooling vessel shown in FIG. 4(A). As shown in FIG. 4(A), the pasteurizer for cooling described as another example of prior art is constructed so as to carry in work 50 at approximately 95° C. and take out the work after cooling to approximately 40° C. A first cooling vessel 60a, a second cooling vessel 60b, a third cooling vessel 60c, a fourth cooling vessel 60d, a fifth cooling vessel 60e and a last cooling vessel 60f are disposed between the upstream side from which the work are carried in and the downstream side to which the cooled work are taken out and the work 50 are finally cooled in the last cooling vessel 60f by spraying a pure water for cooling 65.

A cooling tower 63 is disposed at the outside of the cooling vessels. A cold heat energy obtained from the air outside through the cooling tower and a cold heat energy, obtained by a heat exchanger 62, of the pure water for cooling supplied to the last cooling vessel 60f are given to the first, the second and the third cooling vessel 60a, 60b, 60c by a heat exchanger 64 so as to cool the work through each cooling vessel. As shown in FIG. 4(B), the temperature of the work 50 is gradually decreased from 95° C. to 55° C. while passing through from the inlet of the first cooling vessel 60a to the outlet of the third cooling vessel 60c and finally is decreased in the last cooling vessel by approximately 15° C. to take out the work under the lowered temperature of 40° C. The construction is a minimum-drainage, energy-saving and water-saving type.

Meanwhile, a pasteurizer for sterilization having a sterilizing function by a heat energy in the conveying process have been hitherto utilized in comparison to the pasteurizer for cooling having a cooling function without a sterilizing function as shown in FIG. 3 and FIG. 4.

As a pasteurizer for sterilization as mentioned above, the type shown in FIG. 5 is publicly known.

Figure 5A:
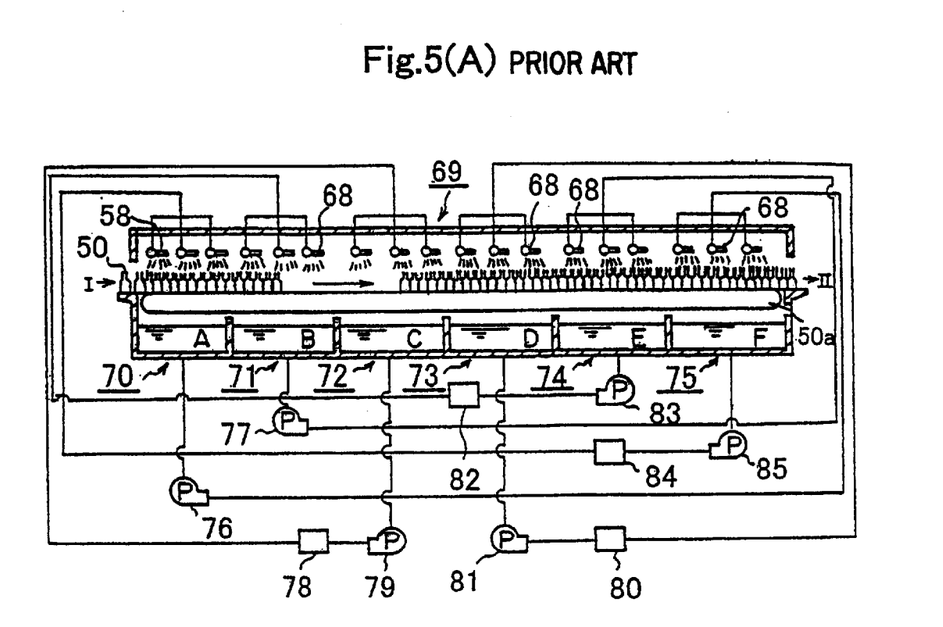
FIG. 5(A) is a schematic drawing of a pasteurizer for sterilization of prior art. (B) is a graph depicting a temperature distribution of (A).

FIG. 5(A) schematically illustrates the construction of the pasteurizer. The pasteurizer comprises a tunnel type continuous liquid spraying heat exchanger 69 and a conveyer 50a, the tunnel type continuous liquid spraying heat exchanger 69 being provided from the upstream I to the downstream II in order with heat exchanging chambers for preheating 70 and 71 which form preheating region, heat exchanging chambers for sterilization 72 and 73 which form sterilizing region and heat exchanging chambers for gradual cooling 74 and 75 which form gradually cooling region in order, the conveyer 50a loading and conveying work 50 thereon in the heat exchanger.

Each heat exchanging chamber for preheating, heat exchanging chamber for sterilization and heat exchanging chamber for gradual cooling have liquid spraying parts 68 capable of spraying to the work 50 on the conveyer and have liquid storage trays disposed under the conveyer and capable of storing spraying liquid therein. The pasteurizer has a construction capable of transporting the spraying liquid under a pressure through appropriate heating devices by pumps so that a temperature distribution of the stored liquid forms a pattern shown in FIG. 5(B).

Figure 5B:
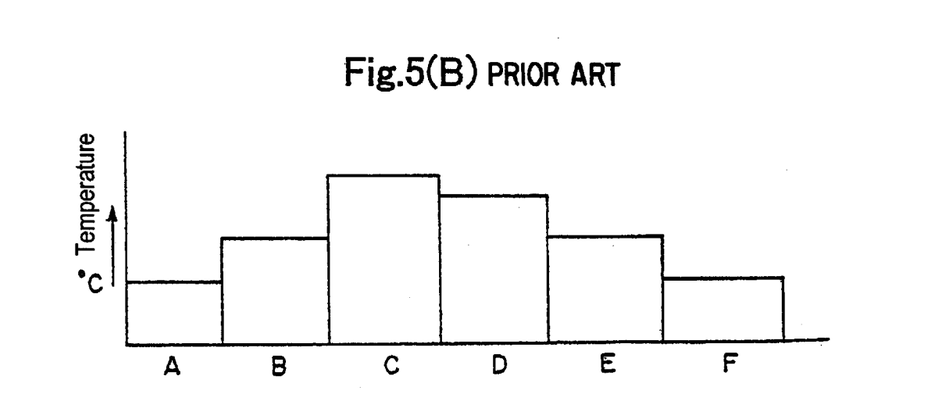

Namely, for an example, the spraying liquid in the liquid storage tray A is transported under a pressure to the spraying part of the heat exchanging chamber for gradual cooling F by the pump 76, the spraying liquid in the liquid storage tray B is transported under a pressure to the spraying part of the heat exchanging chamber for gradual cooling E by the pump 77, the spraying liquid in the liquid storage tray C is transported under a pressure to the spraying part of the heat exchanging chamber for sterilization C through the heating device 78 by the pump 79, the spraying liquid in the liquid storage tray D is transported under a pressure to the spraying part of the heat exchanging chamber for sterilization D through the heating device 80 by the pump 81, the spraying liquid in the liquid storage tray E is transported under a pressure to the spraying part of the heat exchanging chamber for preheating B through the heating device 82 by the pump 83 and the spraying liquid in the liquid storage tray F is transported under a pressure to the spraying part of the heat exchanging chamber for preheating A through the heating device 84 by the pump 85 so as to form the aforementioned temperature distribution pattern.

In case the transportation of work is interrupted during the operation by a certain cause, the temperature of the stored liquid rises or declines because the work cease to deprive of or give heat to result in a problem of unusual rising of temperature of the work during transportation or destruction of the containers such as cans, bins and so forth. The invention of a pasteurizer having sterilizing function by an efficient heat energy together with the countermeasure to the no-load state was presented as a title of "Pasteurizer for countermeasure to no-load state" by the present inventors and disclosed in Japanese Patent publication 10-273117.

Figure 6:
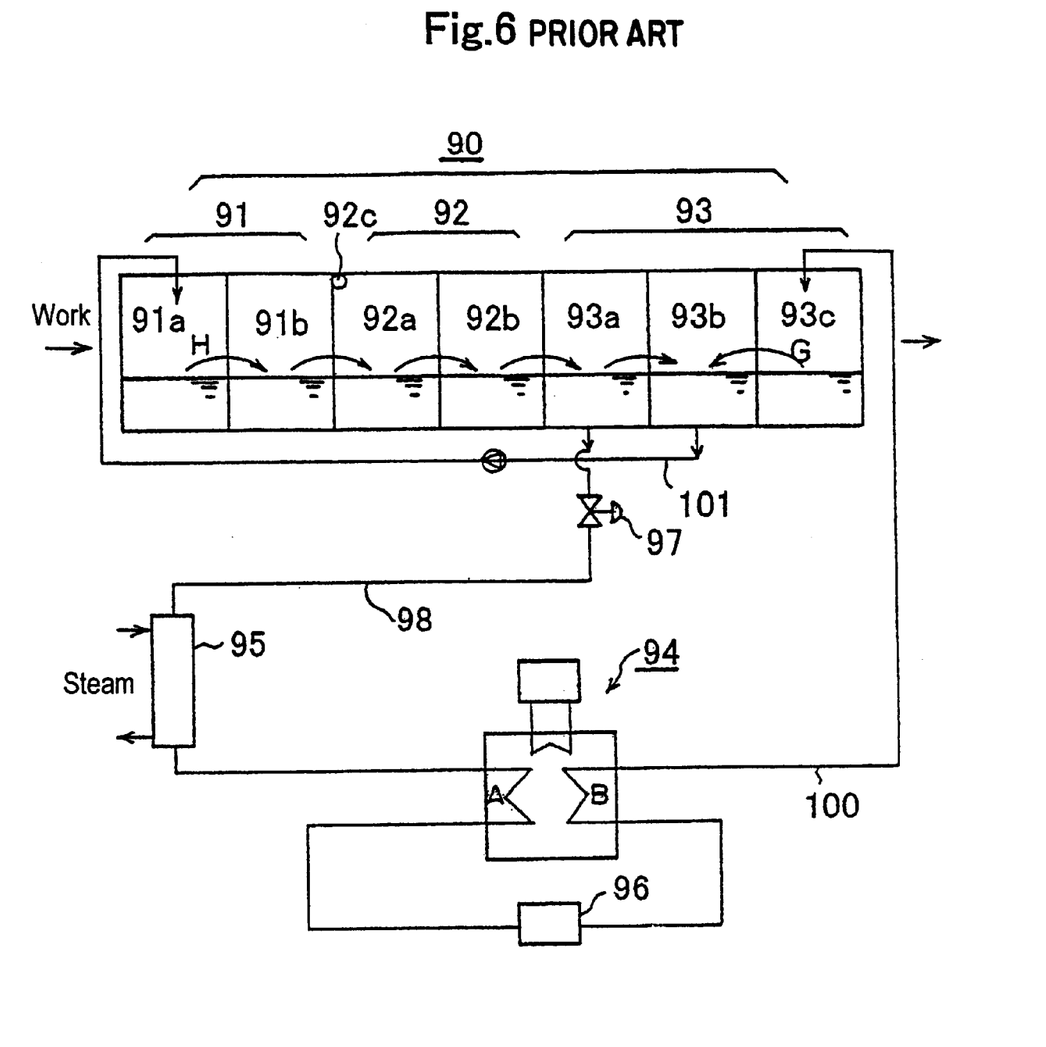
FIG. 6 is a schematic drawing of a pasteurizer for sterilization having no-load state of prior art.

The schematic construction of a pasteurizer for no-load state utilizing an adsorption freezing machine as a first example of the above mentioned pasteurizer for no-load state is explained using FIG. 6.

Figure 7:
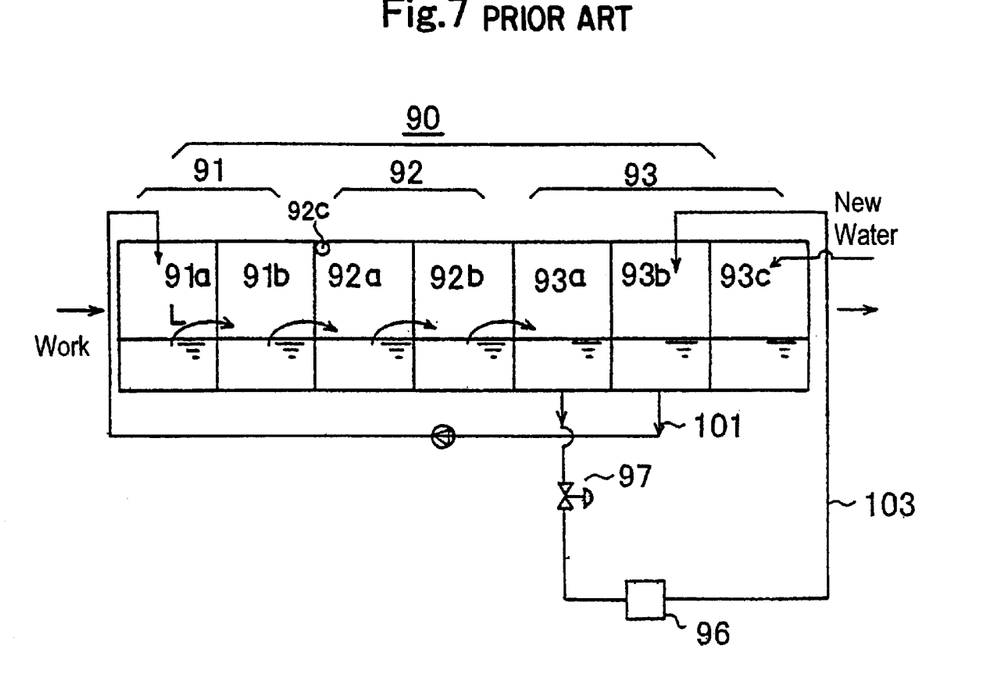
FIG. 7 is a schematic drawing of a pasteurizer for sterilization having no-load state of prior art as another example.

FIG. 7 shows the schematic construction of a pasteurizer utilizing a cooling tower as a second example.

Figure 8:
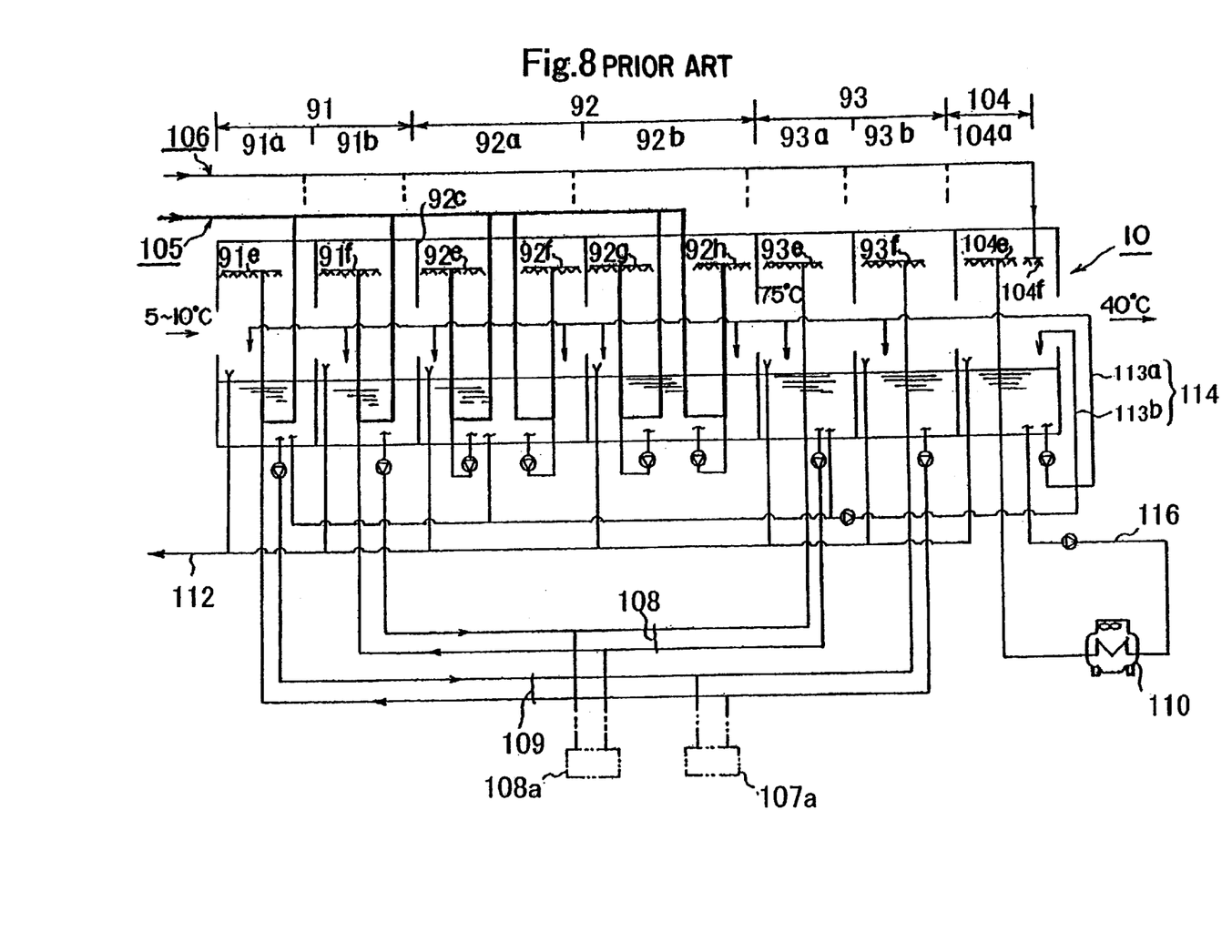
FIG. 8 is a schematic drawing of a pasteurizer for sterilization having no-load state of prior art as another example.

FIG. 8 shows the schematic construction of a pasteurizer having hot water sprayers by steam bubbling, a countercurrent circulating path with heat exchanger for cooling of no-load state, a rinse function for economizing new water and a parallel circulating path for replenishing water to each storage tray as a third, a fourth and a fifth example.

As shown in FIG. 6, a first example of a pasteurizer for no-load state utilizing the adsorption type freezing machine according to the proposal comprises a pasteurizer 90, a heating device 95, an adsorption type freezing machine 94, a cooling tower 96, a return flow path 101 through which water is pumped under pressure from a storage tray of a heat exchanging chamber for gradual cooling 93b at the downstream side to a gradually cooling region 93 to a spraying part of a heat exchanging chamber for preheating 93b at the downstream side to a preheating region 91.

The pasteurizer 90 comprises the preheating region 91, the sterilizing region 92 and the gradual cooling region 93. The preheating region 91 comprises heat-exchanging chambers for preheating 91a and 91b. The sterilizing region 92 comprises heat-exchanging chambers for sterilizing 92a and 92b. The gradually cooling region comprises heat-exchanging chambers for gradual cooling 93a, 93b and 93c.

The heat exchanging chambers for preheating 91a and 91b comprise spraying parts for spraying preheated spraying water to work and storage trays for receiving preheated spraying water, the heat exchanging chambers for sterilizing 92a and 92b comprise spraying parts for spraying hot water to the work and storage trays for receiving hot spraying water and, the heat exchanging chambers for gradual cooling 93a, 93b and 93c comprise spraying parts for spraying gradually cooling water to the work and storage trays for receiving gradually cooling spraying water in order to take out the work after preheating, heating, sterilizing and cooling gradually.

An element for detecting no-load state 92C is disposed at the inlet of the upstream side of the sterilizing region 92. When a no-load state is detected, a hot storing water of the heat-exchanging chamber for gradual cooling 93a is led to the adsorption-freezing machine 94 and the cooling tower 96 through a leading path 98 and the heater 95 by activation of an electromagnetic valve 97 to be deprived of the heat of the water. Then the heat deprived water is returned to the storage tray of the heat exchanging chamber for gradual cooling 93C by the spraying part thereof through a return route of the heat deprived water 100.

The returned heat-deprived water flows through an overflow stream G to the storage tray of the heat exchanging chamber 93b and then is led to the storage tray of the heat-exchanging chamber for preheating 91a by the spraying part thereof through a return path 101. In addition to that, a closed cycle is formed by overflow stream of the direction of the arrow L through each storage tray of the heat exchanging chamber for preheating 91b, the heat exchanging chambers for sterilizing 92a and 92b and the heat exchanging chamber for gradual cooling 93a so as to be capable of adjusting the temperature of stored water of a series of the storage trays.

FIG. 7 shows a schematic construction of a pasteurizer utilizing a cooling tower as a second example of a pasteurizer for no-load state disclosed in Japanese Patent publication 10-273117.

In this example, it is designed to cool and adjust the temperature of stored water by depriving of heat from hot stored water, the temperature of which rises because of interruption of carrying in work at no-load state. A return path for deprived heat 103 comprising a detecting element for detecting no-load state 92C, a return flow path 101, an electromagnetic valve 97 and a cooling tower 96 is disposed to a pasteurizer having the same construction as the first invention 90 so as to avoid unusual rising of temperature of the work caused by interruption of carrying in the work.

In case of the above construction, when the detecting element for detecting no-load state 92C is activated, the activation actuates the electromagnetic valve 97 so that the hot stored water of the heat exchange chamber for gradual cooling is led to the cooling tower 96 and is deprived of heat. The heat-deprived water is returned to the heat-exchanging chamber for gradual cooling by way of a deprived heat return path 103.

The returned heat deprived water is led to the storage tray of the heat exchanging chamber for preheating 91 a by the spraying part thereof through the return path 101. In addition to that, a closed cycle is formed by overflow stream of the direction of the arrow L through each storage tray of the heat exchanging chamber for preheating 91b, the heat exchanging chambers for sterilizing 92a and 92b and the heat exchanging chamber for gradual cooling 93a so as to be capable of adjusting the temperature of stored water of a series of the storage trays.

On this occasion, an appropriate amount of new water may be led to the heat exchanging chamber for gradual cooling FIG. 8 shows a schematic construction of a pasteurizer for no-load state having hot water sprayers by steam bubbling, a countercurrent circulating path with a heat exchanger for cooling of no-load state, a rinse function for economizing fresh water and a parallel circulating path for replenishing water to each storage tray as a third, a fourth and a fifth example disclosed in Kokai publication 10-273117.

As shown in FIG. 8, the pasteurizer 90 in the first, the second and the third examples comprises heat exchanging chambers for preheating 91a and 91b, which form a preheating region 91, heat exchanging chambers for sterilizing 92a and 92b, which form a sterilizing region 92, heat exchanging chambers for gradual cooling 93a and 93b, which form a gradually cooling region 93, a heat exchanging chamber 104a of the most downstream region 104 and an unshown passing-through conveyer for transporting work.

Spraying parts 91e and 91f of the preheating region 91 for spraying hot water, heated by steam bubbling, or cooling water to the work on the conveyer for transporting, spraying parts 92e, 92f, 92g and 92h of the sterilizing region 92, spraying parts 93e and 93f of the gradual cooling region 93 and spraying parts 104e and 104f of the most downstream region 104 are disposed at the upper parts in the heat exchanging chambers. Storage trays, which receive spraying water sprayed from each spraying part, are disposed under the conveyer.

A hot water of a designated temperature is made by joining a steam supplied from a steam-heating source 105 with the spraying water pumped up from the storage tray at a steam bubbling part while adjusting the amount of bubbling steam with an automatic control valve disposed at each steam bubbling part. The hot water thus obtained is sprayed to the work.

In this case, the stored water does not need to be so hot at the starting point of the operation as in case of the conventional method because the temperature is determined by the amount of the bubbling steam, so that the waiting time is unnecessary and heat loss while waiting that exist in the prior art can be diminished to a minimum.

Fluctuation of the load can also be freely coped with by adjusting the amount of steam or operating off and on the supplying of the steam.

Further, countercurrent circulating paths 107, 108 are disposed between the heat-exchanging chamber for gradual cooling 93a and the heat-exchanging chamber for preheating 91b and between the heat-exchanging chamber for gradual cooling 93b and the heat-exchanging chamber for preheating 91a. The reverse flow circulating paths have heat exchangers for cooling 107a, 108a, which are used in a no-load state such as an uneven load state.

In case of the countercurrent circulating path 107, for example, the water warmed in the heat-exchanging chamber for gradual cooling 93b is pumped up through the countercurrent circulating path 107 and is sprayed from the spraying part 91e of the heat-exchanging chamber for preheating 91a so as to deprive the 5–10° C. work of cold heat and to return to the spraying part 93f in the heat-exchanging chamber in order to utilize heat efficiently and to economize new water by restraining from using excess new water in the gradually cooling region 93.

In the heat-exchanging chamber 104a of the most downstream region 104, a spraying part 104f spraying new water (of approximately 20° C.) for rinsing by being supplied from a new water replenishing part 106 and a spraying part 104e spraying cooling water for rinsing through a cooling water circulating path 116, which cools stored water to a designated temperature by pumping up to the cooling tower 110 from the lower storage tray, are disposed in order to suppress the amount of new water used for rinsing.

The water in the storage trays in upstream side becomes insufficient because the work are sprayed with water in the upstream and carry a part of the sprayed water to the down stream so as to be necessary to replenish water. In the heat-exchanging chamber 104a of the most downstream region, a parallel replenishing-water supplying circulating path 114 comprising a replenish-piping part 113a and a return-piping part 113b is disposed so as to supply water individually through the replenish-piping part 113a with the parallel path while controlling the temperature of the water by detecting the temperature and the level of the water in each tray. The water temperature of each storage tray is capable of being controlled, in addition to replenishing an adequate amount of new water, by circulating water to the storage tray of the heat-exchanging chamber 104a while keeping the water level by the return-piping part 113b.

Further, a drainage 112 is disposed so that an appropriate drainage from the preheating region and gradual cooling region is possible.

The element for detecting no-load state 92C is disposed at the upstream side inlet of the sterilizing region 92. The temperature is detected at the inlet of the sterilizing region where, as hot water is sprayed, it is susceptible to influence of heat by interruption of the carried-in work.

By aforementioned operation, it is so constructed that unsterilized products canned or binned with such as juice, light-carbonated fruit drink, milk or Calpico are carried in as a state of 5–10° C. to the pasteurizer, are concluded the sterilization at the temperature of 75° C. and are taken off as a state of approximately 40° C.

Figure 9:
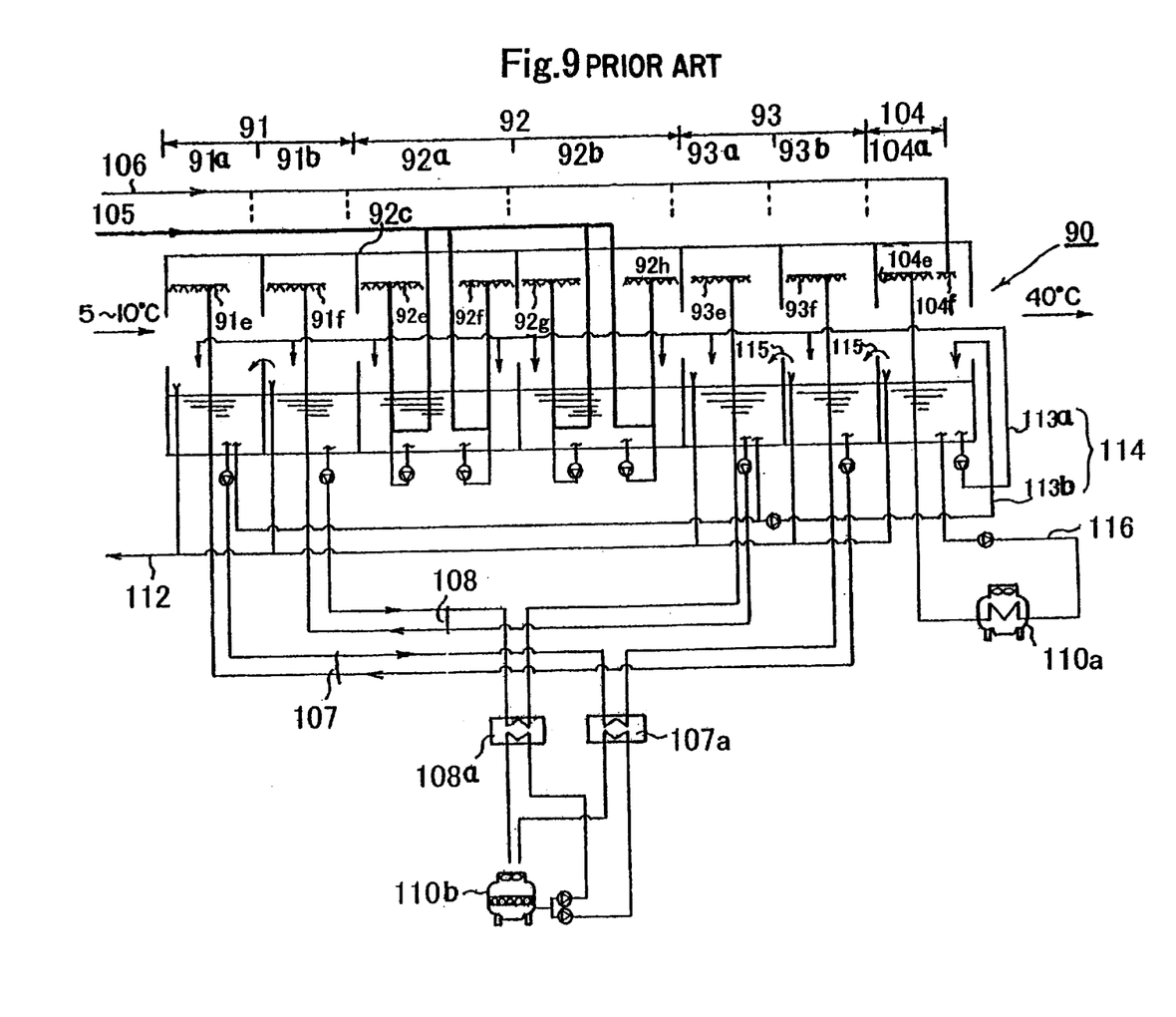
FIG. 9 is a drawing depicting a state of operation of each constructed part in case of an uneven load state of the pasteurizer shown in FIG. 8.

FIG. 9 shows an operation state of each constructed part shown in FIG. 8 at the time of an uneven load state. The above operation state at the time of an uneven load state indicates the case of no work in the heat-exchanging chambers for preheating 91a and 91b. In case of the uneven load state, when hot water is sprayed, steam is not bubbled into the spraying parts 91e and 91f of the heat-exchanging parts 91a and 91b but steam is bubbled only into the spraying parts 92e, 92f, 92g and 92h of the heat exchanging chamber for sterilizing.

The spraying part 91e sprays warm water warmed by spraying the stored water of the storage tray 93b of the heat-exchanging chamber for gradual cooling 93b to the work through the countercurrent circulating path 107. The spraying part 91f sprays warm water warmed by spraying the stored water of the storage tray 93a of the heat-exchanging chamber for gradual cooling 93a to the work through the countercurrent circulating path 108.

For there are work for preheating in the preheating region in case of no uneven load state, the spraying water from the spraying parts 91e and 91f deprives cold heat energy of the work to give and take the heat between the gradual cooling region 93 and the preheating region 91. Since there are no work at the region, a lot of new water is necessary in the gradual cooling region because of unbalance of heat.

With this regard, in the present invention, heat exchangers for cooling 107a and 108a having a cooling tower 110b are disposed in the countercurrent circulating path 107, 108 in order to avoid the usage of a plenty of new water in the gradual cooling region by compensate the unbalance of heat.

In this case, the stored water (new water and circulating water for gradual cooling) of the heat-exchanging chamber 104a of the most downstream region 104 is transported to the heat-exchanging chamber for gradual cooling by an overflow 115 to make good use of the cold heat energy. A parallel replenishing- water supplying circulating path 114 operates in the same as the aforementioned way. A drain 112 is drained only by overflow of new water.

When an element for detecting no-load state 92C is activated, an electromagnetic valve for bubbling steam to the spraying parts 91e and 91f of the preheating region 91, which is not shown in the figure, operates to shut the flow of steam and to put the heat exchanger for cooling 107a and 108a activated.

Meanwhile, when the transportation of the work, which have been continuously carried in, is interrupted by a certain cause under operation, heat of the work is not taken or given so that the temperature of storage liquid in cooling chambers disposed in the course of transportation of the work between a carry-in port and a take-out port rises remarkably, which gives an increase to an unusual temperature change to the work, therefore a certain measure is required.

In order to sterilize the work through the heat treatment process of preheating, heating, sterilizing, precooling and cooling, the work are carried in to the pasteurizer at a state of normal temperature of approximately 30° C., held for a prescribed time at a sterilizing temperature of 70° C. and cooled gradually to an normal temperature of approximately 30° C. Consequently, a large quantity of water is used as a heat-exchanging medium and a lot of heat is consumed so that there leaves much to be desired to be improved from the viewpoint of energy-saving and water-saving.

DISCLOSURE OF INVENTION

The present invention has done in the light of aforementioned problem and has an object of offering an energy-saving and water-saving type pasteurizer for cooling and pasteurizer for sterilization, which is capable of keeping a stable temperature distribution pattern even if transporting of work is interrupted while operation.

In case the present invention is functioned as a pasteurizer for cooling, in a pasteurizer for cooling having a countercurrent means which flows reversely a rinse water sprayed in a cooling vessel of end side existing in the most downstream side to a cooling vessel of upstream side utilizing overflow function or circulating-spraying and cooling function in order to cool work containers such as cans and bins and so forth filled with product liquid, after high-temperature sterilization, by carrying in one after another to a plural cooling vessels disposed in serial array, the present invention is directed to a pasteurizer which is characterized by having:

an adsorption freezing machine between a high temperature cooling vessel disposed at carried-in side of work containers and a low temperature cooling vessel disposed at downstream side wherein a cooling liquid obtained by supplying a stored liquid of the high temperature cooling vessel of carry-in side as a heating source liquid to said adsorption freezing machine disposed at the downstream side; and a means for halting or flowing liquid to stop supplying said heating source liquid in case of no-load.

The present invention is directed to a pasteurizer comprising:

a tunnel type conveyer transporting cooling device in which cooling vessels are disposed in serial array wherein high temperature work such as cans, bins and so forth filled a high temperature sterilized product are gradually cooled from a high temperature state of immediately after filling of approximately 75° C. to a low temperature state of approximately 25° C. and are taken out, the cooling device including:

a countercurrent cooling means having a circulating-spray cooling function which supplies the rinse water to the most downstream cooling vessels by spraying and an overflow function which flows reversely the supplied cooling liquid from the downstream side to the upstream side whereby the carried-in high temperature work are gradually cooled by circulating-spray cooling through each stored liquid of from the carry-in side high temperature cooling vessel to the taken-out side low temperature cooling vessel.

Further, as a means for enhancing cooling efficiency, the adsorption freezing machine is disposed between the high temperature side cooling vessel of carried-in-work side and the low temperature side cooling vessel of taken-out-work side wherein, when loaded by the carried-in high temperature work, the stored liquid of the high temperature side cooling vessel is used as a heating source liquid in order to utilize efficiently the temperature difference between the heating source side and the cooling side and the cold heat obtained at the cooling side is utilized as a cooling source for the low temperature side cooling vessel, while at no-load state, the aforementioned heating source liquid is stopped to be supplied and the freezing machine is also stopped to operate so as not to reduce uselessly the temperature of the stored liquid of the high temperature cooling vessel. The construction is for countermeasure to no-load state.

Further, in a pasteurizer for cooling having a countercurrent means which flows reversely a rinse water sprayed in a cooling vessel of end side existing in the most downstream side to a cooling vessel of upstream side utilizing overflow function or circulating-spraying and cooling function in order to cool work containers such as cans and bins and others filled with product liquid, after high-temperature sterilization, by carrying in one after another to a plural cooling vessels disposed in serial array, a pasteurizer of the present invention is characterized by having:

a cooling tower disposed between the high temperature side cooling vessel at the relatively upstream side position along the cooling direction of the work containers and the cooling vessel at the downstream side thereof; and a means for halting or flowing a liquid to stop supplying said heating source liquid in case of no-load while, when loaded by the carried-in work containers, the stored liquid of the comparatively upstream side cooling vessel is supplied to the downstream side cooling vessel through the cooling tower.

In such construction, the pasteurizer comprises a tunnel type conveyer transporting cooling device in which cooling vessels are disposed in serial array wherein high temperature work such as cans, bins and others filled a high temperature sterilized product are gradually cooled from a high temperature state of right-after-filling of approximately 75° C. to a low temperature state of approximately 25° C. and taken out, said cooling device including:

a countercurrent cooling means having a circulating-spray cooling function which supplies the rinse water to the most downstream cooling vessels by spraying and an overflow function which flows reversely the supplied cooling liquid from the downstream side to the upstream side whereby the carried-in high temperature work are gradually cooled by circulating-spray cooling through each stored liquid of from the carried-in side high temperature cooling vessel to the take-out side low temperature cooling vessel.

As a means for enhancing cooling efficiency, a cooling tower is disposed between the high temperature side cooling vessel at the comparatively upstream side position along the cooling direction of the work containers and the cooling vessel at the downstream side.

The stored liquid of the high temperature side cooling vessel flowed reversely therethrough by a countercurrent means such as the overflow function or the circulating-spray cooling function and others is cooled by the air outside and returned to the low temperature side cooling vessel so as to replenish cold heat energy.

Further, the pasteurizer has a construction for no-load state by which the stored liquid of the high temperature side cooling vessel is stopped to be supplied to the cooling tower in a state of no-load.

In the present invention, in a pasteurizer for cooling having a countercurrent means which flows reversely a rinse water sprayed in a cooling vessel of end side existing in the most downstream side to a cooling vessel of upstream side utilizing overflow function or circulating-spraying and cooling function in order to cool work containers such as cans and bins and so forth filled with product liquid, after high-temperature sterilization, by carrying in one after another to plural cooling vessels disposed in serial array, a pasteurizer is provided with:

an adsorption freezing machine between a high temperature cooling vessel disposed at carry-in side of work containers and a low temperature cooling vessel disposed at downstream side; and a cooling tower disposed between the high temperature side cooling vessel at the relatively upstream side position along the cooling direction of the work containers and the cooling vessel at the downstream side thereof.

According to the invention, the pasteurizer comprises a tunnel type conveyer transporting cooling device in which cooling vessels are disposed in serial array wherein high temperature work such as cans, bins and so forth filled a high temperature sterilized product are gradually cooled from a high temperature state of immediately-after-filling of approximately 75° C. to a low temperature state of approximately 25° C. and taken out, said cooling device including:

a countercurrent cooling means having a circulating-spray cooling function which supplies the rinse water to the most downstream cooling vessels by spraying and an overflow function which flows reversely the supplied cooling liquid from the downstream side to the upstream side whereby the carried-in high temperature work are gradually cooled by circulating-spray cooling through each stored liquid of from the carried-in side high temperature cooling vessel to the take-out side low temperature cooling vessel.

Further, as a means for enhancing cooling efficiency, the adsorption freezing machine is disposed together with the cooling tower.

Thus, in addition to an adsorption freezing machine which is provided between a high temperature cooling vessel disposed at carry-in side of work containers and a low temperature cooling vessel disposed at downstream side near taken-out side, a cooling tower is also provided between the high temperature side cooling vessel of the upstream side and the low temperature side cooling vessel at the downstream side thereof, which are in a group of intermediate cooling vessels existing between cooling vessels connected through the adsorption freezing machine.

The pasteurizer is also designed to correspond to no-load state therefore,under the state of such, the supply of the heat source liquid to the adsorption freezing machine and the supply of the stored liquid of the high temperature side cooling vessel to the cooling tower are stopped by means of halting or flowing liquid.

In each aforementioned invention, a cold heat energy of the downstream side cooling vessel in a group of the cooling vessels is supplied to the primary side of a heat exchanger so as to make capable of supplying a cold heat energy from the secondary side thereof as a cold heat energy spraying liquid to the adjacent upstream side cooling vessel while circulating to the storage tray of the same temperature as the primary side stored liquid which is heated by giving cold heat energy.

The aforementioned inventions region pateurizer utilizing the adsorption freezing machine, a pateurizer utilizing the cooling tower or a pasteurizer utilizing the both of the adsorption freezing machine and the cooling tower so as to make capable of supplying a cold heat energy from the secondary side thereof as a cold heat spraying liquid to the adjacent upstream side cooling vessel while circulating to the storage tray of the same temperature as the primary side stored liquid which is heated by giving cold heat.

In case of letting the pasteurizer be functioned as a pasteurizer for sterilization, in a pasteurizer having a preheating region, heating region, sterilizing region, precooling region and cooling region along a transporting path from the upstream to the downstream, the pasteurizer comprises:

a line for supplying a cooling or heating energy which forms and holds each temperature region in the each storage tray;

a cross-linked circulating path for spraying liquid which is formed between a circulating spray liquid of the preheating region sprayed in the precooling region and a circulating spray liquid of the precooling region sprayed in the preheating region;

a line for supplying a low temperature which makes a low temperature circulating spray by supplying a cold heat energy to a heat-exchanging chamber of the cooling region; and a line for replenishing a stored liquid replenishing a stored liquid to an upstream side storage tray by cooling and storing overflow liquid of each storage tray.

The above-mentioned invention brings a sterilizing function to the transportation line of the work. Thus, the work containers such as cans, bins and so forth filled with liquid product are carried in to the pasteurizer at a state of normal temperature of approximately 30° C., sterilized at a prescribed temperature for a prescribed time by a high temperature spraying at approximately 70° C. and followed by a prescribed cooling to take out the work at a normal temperature of approximately 30° C.

As stated above, a preheating region, heating region, sterilizing region, precooling region and cooling region are disposed in series from the upstream to the down stream wherein the transporting work are sequentially preheated, heated, sterilized, precooled and cooled with heat-exchanging function of giving and taking heat by high temperature heat spraying or low temperature heat spraying of heat medium to the carried-in work of normal temperature.

In each region, a spraying part of high temperature heat spraying or low temperature heat spraying for giving and taking heat and a liquid storage tray which receives the sprayed liquid through the work thereunder and performs circulating-spraying by supplying the spraying liquid of a prescribed temperature are disposed so as to give and take heat.

In the pasteurizer having above-mentioned construction, the pasteuriser has a line for supplying cold heat or heat energy in order to set the temperature of stored liquid of a storage tray disposed at each region.

Further, it is so constructed that the stored liquid is circulated in cross-linked wise between the storage tray of the preheating region and the storage tray of the precooling region so as to circulate the spraying liquid whose temperature has risen after cooling the work in the preheating region.

By this construction, in case the heat for treating the work used in the storage tray of the precooling region is equal to that of preheating region, heating energy for heating or cold heat for cooling is not necessary to supply so as to contribute to saving energy.

Further, it is so constructed that a normal temperature of approximately 30° C. is prepared by spraying circulatively a low temperature cooling liquid in the cooling region so as to easily treat the work after taking-out.

Further, it is so constructed that overflow liquid of each storage tray is gathered in a tank, cooled to prescribed extent and supplied to the upstream side storage tray as a stored liquid in order to compensate the reduction of water level of the upstream side in comparison to the downstream side because spraying liquid is held on the work to transport to the downstream in the storage tray of each region so as to contribute saving water.

Further, according to the present invention, a ratio of heat treating time of preheating, heating, sterilizing, precooling and cooling is preferably 1:1:2:1:1.

By the above time allotment, the transporting work stay in the sterilizing region for a long time to take enough time of sterilization so as to be able to sterilize perfectly.

Further, concerning the line for supplying a cooling or heating energy, it is preferable to use water as a spraying liquid and a storage liquid and to use a water supplying line which supplies cold heat and a steam supplying line which supplies heating energy.

With the above construction, for setting the temperature of the stored liquid of each storage tray, it is so constructed that water is used as a stored liquid and steam or water is optionally used so as to adjust and hold to a prescribed temperature.

Further, it is preferable to construct so that cold heat is supplied from a cooling part which supplies cold heat to the line for supplying a low temperature and the line for replenishing the stored liquid through the cooling tower.

With the above construction, cold heat for the low temperature circulating-spraying used for cooling the work of the cooling region and cold heat used in the line for replenishing the stored liquid are in charge of the cooling part consisting of an energy saving construction which is dependent on the taking heat by the cooling tower.

DETAILED DESCRIPTION OF PREFERRED EMBODIMENTS

The invention will now be described by way of example with reference to the accompanying drawings. However the description herein of specific embodiments such as to the dimensions, the kinds of material, the configurations and the relative disposals of the elemental parts and the like is not intended to limit the invention to the particular forms disclosed but the intention is to disclose for the sake of example unless otherwise specifically described.

Figure 1:
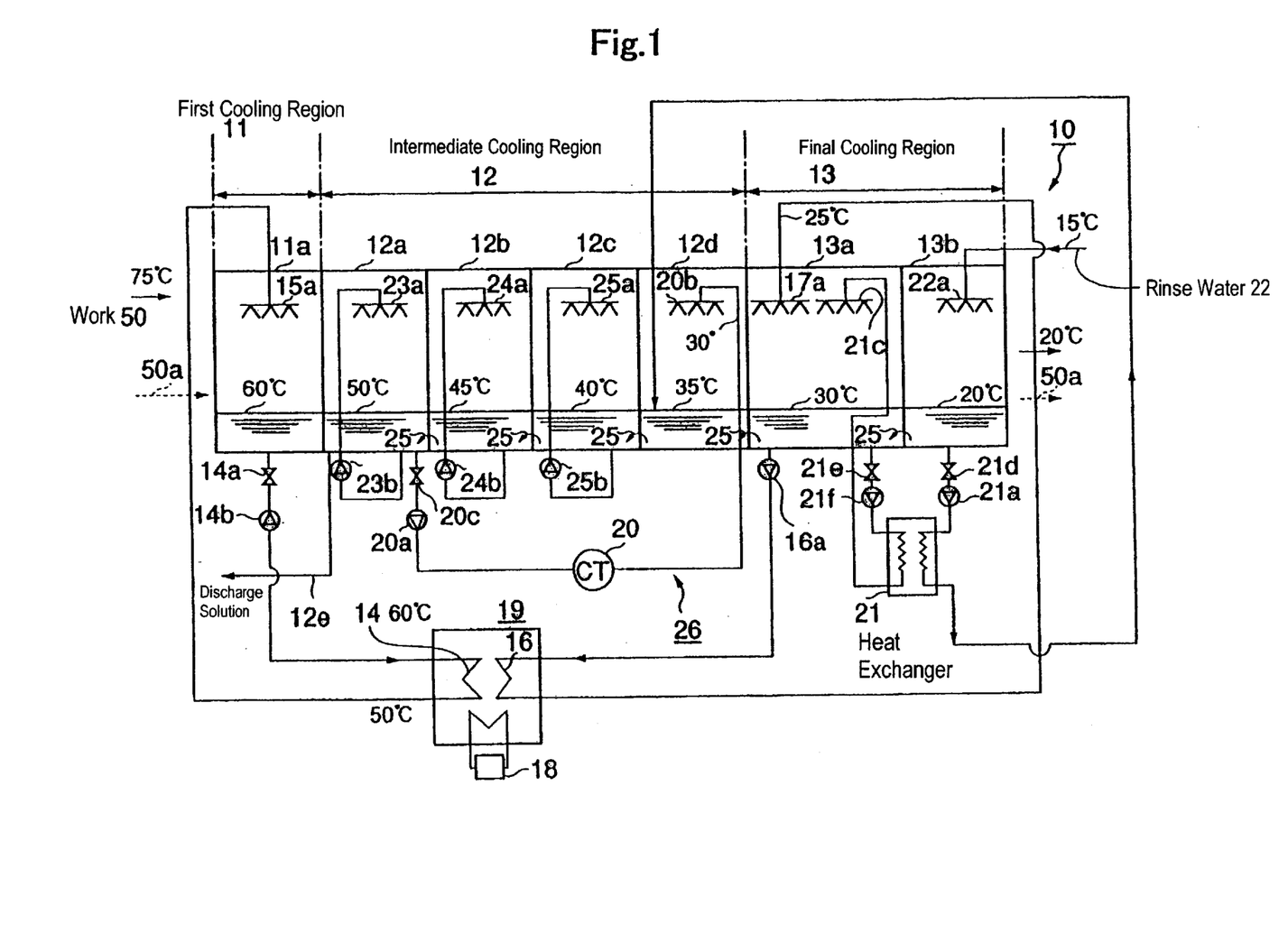
FIG. 1 is a schematic drawing of a pasteurizer for cooling as a first example of the present invention.

FIG. 1 is a schematic drawing of a pasteurizer for cooling according to an example of the present invention.

As shown in FIG. 1, according to the present invention, a pasteurizer for cooling having no-load state comprises a tunnel type cooling device 10 wherein high temperature work such as cans, bins and so forth filled a high temperature sterilized product are carried in on a conveyer 50a and are gradually cooled from a high temperature state of approximately 75° C. to a low temperature state of approximately 25° C., said cooling device including:

Plural cooling vessels 11a, 12a, 12b, 12c, 12d, 13a and 13b which take heat of the work to cool and are disposed in serial array from the upstream side to the downstream side whereby a first cooling region 11, an intermediate cooling region 12, a final cooling region 13 are formed;

an adsorption freezing machine 19 disposed between the first cooling region 11 and the final cooling region 13; and a cooling tower 20 disposed at the intermediate cooling region 12.

In the most downstream cooling vessel 13b of the final cooling region 13, a cooling solution rinse water 22 of approximately 15° C. is sprayed to transporting work 50 by a spraying part 22a. The cooling solution whose temperature rises to approximately 20° C. as a result of spraying overflows consecutively to the adjacent upstream side cooling vessels by an overflow stream 25 and takes heat of the high temperature work which are transported from the upstream to form an approximate temperature distribution of 20° C.→30° C.→35° C.→40° C.→45° C.→50° C. A part of the stored liquid, whose temperature rises up to 50° C., of the most upstream cooling vessel 12a of the intermediate cooling region 12 is discharged to the outside as a drain water 12b.

The adsorption type freezing machine 19 is disposed between the first cooling vessel 11a of the first cooling region 11 and the upstream side cooling vessel 13a of the final-cooling region 13 wherein a high temperature stored liquid of approximately 60° C. at loaded state is supplied to a heat source side heat exchanger 14 of the freezing machine by a pump 14a as a heat source water and said stored liquid whose temperature drops as a result of supplying heat to the said heat exchanger 14 is sprayed to immediately-after-carried-in work 50 of approximately 75° C. to cool the work to a temperature of approximately 60° C. while the sprayed liquid raised to approximately 60° C. in temperature is returned to the heat source side of the adsorption freezing machine as a heat source liquid.

In the adsorption type freezing machine 19, the adsorbent of the adsorption freezing machine is reproduced. A condenser 18 condenses released steam. The condensed cooling medium is vigorously evaporated. The heat of evaporation generated therefrom is supplied to a cooling side heat exchanger 16 as a cold heat.

The stored liquid of approximately 30° C. in the upstream side cooling vessel 13a of the final cooling region 13, which is delivered by a pump 16a, is cooled to approximately 25° C. by the cold heat released by said cooling side. A temperature of the transporting work is lowered to approximately 30° C. by spraying the liquid thereon with a spraying part 17a while the temperature of the stored liquid is maintained at approximately 30° C. by the heat deprivation from the work and the overflow of the downstream side cooling vessel.

A cooling tower 20 is disposed between a most upstream cooling vessel 12a of the region 12 and a most downstream cooling vessel 12d in a intermediate cooling region 12 whereby the stored liquid of approximately 50° C. in the cooling vessel 12a at load state is cooled to approximately 30° C. by the outside atmosphere through the cooling tower 20 and a pump 20a and sprayed on the transporting work from a spraying part 20b to form a spray-cooling circulating path 26 so as to lower the temperature of the work to approximately 35° C. and raise the temperature of the stored liquid to approximately 35° C.

In a cooling vessel 12c, the stored liquid of approximately 35° C. in the cooling vessel 12d is reversely flowed by a overflow 25 and sprayed by a spraying part 25a and pump 25b on the work 50 of approximately 45° C. transported from the upstream so as to lower the temperature of the work to approximately 40° C. and raise the temperature of the stored liquid to approximately 40° C.

In a cooling vessel 12b, the stored liquid of approximately 40° C. in the cooling vessel 12c is reversely flowed by the overflow and sprayed by a spraying part 24a and pump 24b on the work 50 of approximately 50° C. transported from the upstream so as to lower the temperature of the work to approximately 45° C. and raise the temperature of the stored liquid to approximately 45° C.

In a cooling vessel 12a, the stored liquid of approximately 45° C. in the cooling vessel 12b is reversely flowed by the overflow 25 and sprayed by a spraying part 23a and pump 23b on the work 50 of approximately 60° C. transported from the upstream so as to lower the temperature of the work to approximately 50° C. and raise the temperature of the stored liquid to approximately 50° C.

The hot stored liquid of the cooling vessel 12a is returned to the cooling tower 20 as stated above.

Going through the above mentioned process in the intermediate region at load state, the temperature of the work lowered to approximately 60° C. from 70° C. in the first cooling region 11 is cooled gradually to form an approximate temperature distribution of 50° C.→45° C.→40° C.→35° C.

By means of aforementioned construction, the work of approximately 75° C. carried in at load state is cooled to approximately 60° C. by the spray-circulation in the first cooling region and after that, the work of approximately 60° C. are cooled gradually to obtain the work of approximately 20° C. at the take-out side using cooling means including the cooling tower in the intermediate cooling region, by supplying rinse water in the final cooling region and using the adsorption freezing machine disposed between the first cooling vessel and the upstream side cooling vessel in the final cooling region.

The construction is designed for no-load state by preventing lowering the temperature of the stored liquids in the first cooling region 11 and the intermediate cooling region 12 by stopping supply of heat source water to the adsorption freezing machine 19 with a valve 14a and stopping supply of the stored liquid from the cooling vessel 12a to the cooling tower 20 with a valve 20c by means of activation of a detector, which is not shown in the figure, at no-load state.

In the final cooling region 13, a heat exchanger is disposed whereby the cold heat energy of the cooling vessel 13b is supplied to the primary side of the heat exchanger and is transferred from the secondary side to the spraying part 21c of upstream side cooling vessel 13a so as to replenish cold heat energy to the downstream side cooling vessel and to circulate to the storage tray of the same temperature as the temperature of the primary side stored liquid whose temperature has risen by giving cold heat energy.

The figure shows the case of replenishing a deficiency of cooling the residual work accompanied by stopping the operation of the adsorption freezing machine 19 and the cooling tower 20 by means of opening valve 21d and 21e at no-load state.

Figure 2:
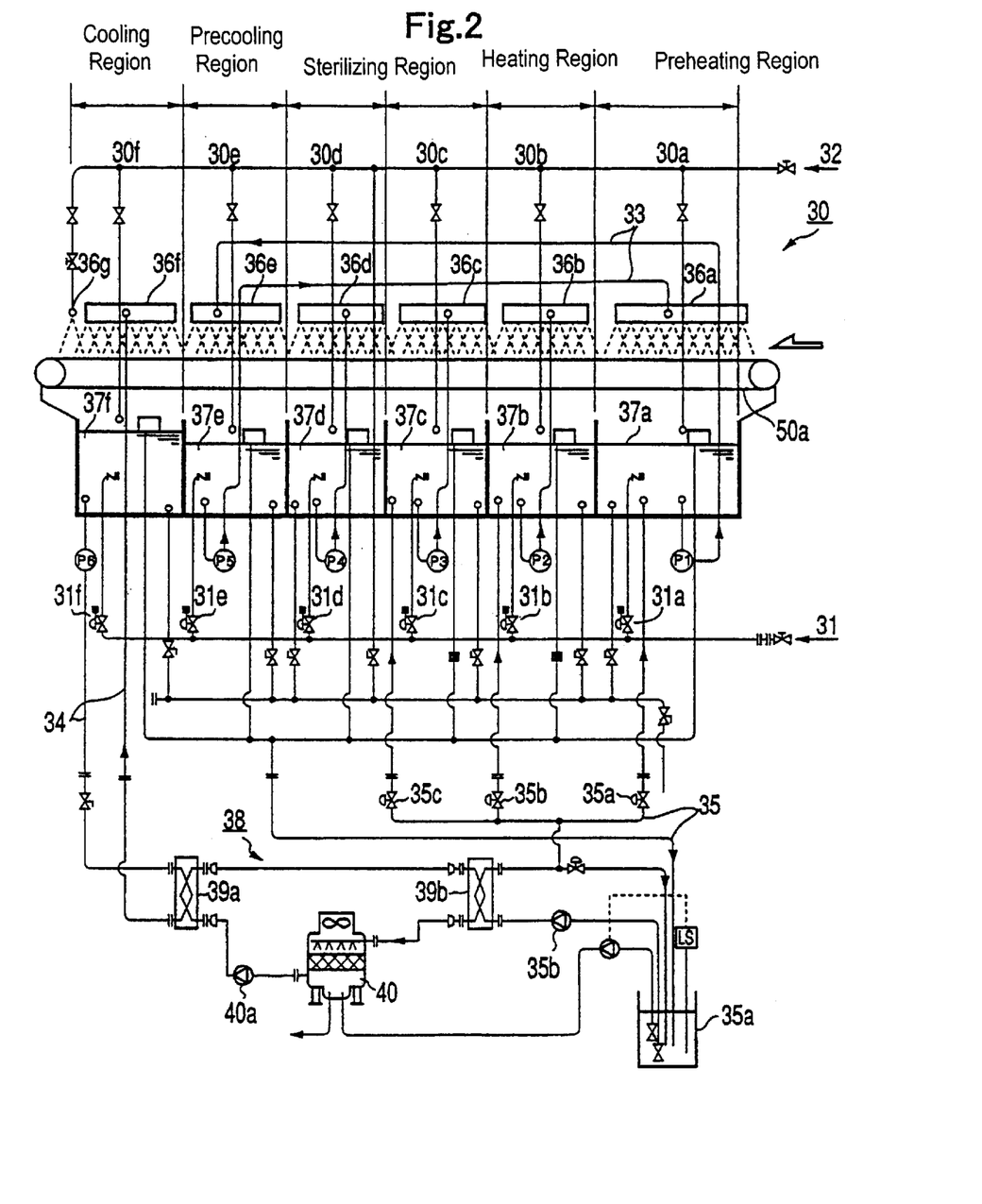
FIG. 2 is a schematic drawing of a pasteurizer for sterilization as a second example of the present invention.

FIG. 2 is a schematic drawing of a pasteurizer for sterilization as a second example of the present invention.

As shown in the figure, a pasteurizer according to the present invention comprises a pasteuriser 30, a line for supplying steam 31 and a line for supplying water 32 as a line for supplying heat and cold heat energy, a cross-linked circulating path 33, a low temperature circulating path 34, a line for replenishing a stored liquid 35, and a heat and cold heat source 38.

A pasteurizer 30 is a pasteurizer for sterilization which comprises a preheating region 30a, a heating region 30b, sterilizing regions 30c, 30d, a precooling region 30e and a cooling region 30f to form heat-exchanging function by further disposing spray parts and storage trays over and under a conveyer for transporting work 50a wherein work of normal temperature of approximately 30° C. are carried in the preheating region 30a passing through the heating region 30b to sterilizing regions 30c, 30d where the work are sterilized at a prescribed temperature of 70° C.~80° C. for a prescribed time and then work are cooled to normal temperature of approximately 30° C. for taking out by passing through the precooling region 30e and the cooling region 30f.

The preheating region 30a includes a spray part 36a and a storage tray 37a and the precooling region 30e includes a spraying part 36e and a storage tray 37e wherein the spraying water heated by cooling the work in the precooling region 30e with the cross-linked circulating path 33 is circulated to spraying part 36a of the preheating region 30a from the storage tray 37e with pumps P5 and P2.

The heating region 30b includes a spraying part 36b and a storage tray 37b, the sterilizing region 30c includes a spraying part 36c and a storage tray 37c and the sterilizing region 30d includes a spraying part 36d and a storage tray 37d wherein a hot water of each storage tray adjusted at a prescribed temperature of approximately 70° C. is sprayed and circulated in each region with pumps P2, P3 and P4.

The cooling region 30f includes a spraying part 36f and a storage tray 37f so as to spray and circulate the stored water of approximately 30° C. through the low temperature circulating path 34 with a pump P6.

An appropriate heating and cold heat energy is supplied from a line for supplying steam 31 and a line for supplying water 32 to each storage tray 37a, 37b, 37c, 37d, 37e, 37f of the preheating region, the heating region, the sterilizing region, the precooling region, the cooling region so as to maintain a prescribed temperature.

Each storage tray has a whole collecting tank 35a which collects overflow water as a whole whereby water is replenished from the tank, after cooling to a proper temperature with a cold heat source 38, which is mentioned thereafter, by a pump 35b and a line for replenishing stored water 35, to the upstream side storage tray whose water level is susceptible to decline because of transferring attached spraying water on the work to the downstream side so as to keep minimum replenishment of new water.

The source of cold heat 38 comprises a cooling tower 40 and heat exchangers 39a, 39b whereby heat is discarded to atmosphere with the cooling tower and thus obtained cold heat energy is supplied to the low temperature circulating path 34 and a line for replenishing stored water 35 by a heat exchanger 39a and 39b respectively.

Pure water for cleaning is sprayed at the way out of the transporting path from a spraying part 36g disposed in the cooling region 30f through the line for supplying water.

A heat balance is made between the preheating region 30a and precooling region 30e by the cross-linked circulating path 33 and the work are cooled in the cooling region with the source of cold heat 38 obtained by the low temperature circulating path 34 and the cooling tower, so that saving energy is effectuated. Saving water is also effectuated by the line for replenishing stored water 35 which is capable of collecting effectively overflowing water.

Industrial Applicability

According to the above-mentioned construction, a pasteurizer for cooling work uses the high temperature stored water formed by deprivation of heat from hot work at load state as a heat source water of a adsorption freezing machine to convert to a cold heat source for cooling a final cooling region and uses cold heat of the outside atmosphere through a cooling tower in a intermediate cooling region so that a energy-saving and water-saving cooling device capable of reducing the consumption of cooling rinse water can be offered while the unusual change of a temperature distribution of stored liquid in each cooling vessels at no-load state can be prevented by stopping the operation of the adsorption freezing machine and the cooling tower together with replenishing cold heat from the final cooling vessel through the heat exchanger so as to be able to transfer to the usual operation immediately when no-load state is dissolved.

Further, as a pasteurizer for sterilizing work containers sterilizes work for a prescribed time after heating from normal temperature to a high temperature and cools again after that, great amount of heat and great amount of water as a heat medium are used according to the prior art. According to the present invention, however, an effective pasteuriser having a large energy-saving and water-saving effect is obtained by a means of acquiring cold heat energy using heat of outside atmosphere, by a means for circulating a stored liquid in which heat balance is devised and by a construction of suppressing replenishing of stored water as far as possible which is a result of setting a prescribed temperature to each storage tray in each region in advance.

What is claimed is:

1. In a pasteurizer having a countercurrent means which flows reversely a rinse water sprayed in a cooling vessel of end side existing in the most downstream side to a cooling vessel of upstream side utilizing overflow function or circulating-spraying and cooling function while work containers such as cans and bins and so forth filled with product liquid, after high-temperature sterilization, are carried in one after another to plural cooling vessels disposed in serial array, a pasteurizer for cooling work containers comprising:

an adsorption freezing machine between a high temperature cooling vessel disposed at carry-in side of work containers and a low temperature cooling vessel disposed at downstream side wherein a cooling liquid obtained by supplying a stored liquid of the high temperature cooling vessel of carry-in side as a heating source liquid to the adsorption freezing machine disposed at the downstream side; and a means for halting or flowing liquid to stop supplying the heating source liquid in case of no-load state.

2. In a pasteurizer having a countercurrent means which flows reversely a rinse water sprayed in a cooling vessel of end side existing in the most downstream side to a cooling vessel of upstream side utilizing overflow function or circulating-spraying and cooling function while work containers such as cans and bins and so forth filled with product liquid, after high-temperature sterilization, are carried in one after another to a plurality of cooling vessels disposed in serial array, a pasteurizer for cooling work containers comprising:

a cooling tower disposed between the high temperature side cooling vessel at the relatively upstream side position along the cooling direction of the work containers and the cooling vessel at the downstream side thereof; and a means for halting or flowing a liquid to stop supplying the heating source liquid in case of no-load while, when loaded by the carried-in work containers, the stored liquid of the comparatively upstream side cooling vessel is supplied to the downstream side cooling vessel through the cooling tower.

3. In a pasteurizer having a countercurrent means which flows reversely a rinse water sprayed in a cooling vessel of end side existing in the most downstream side to a cooling vessel of upstream side utilizing overflow function or circulating-spraying and cooling function while work containers such as cans and bins and so forth filled with product liquid, after high-temperature sterilization, are carried in one after another to a plural cooling vessels disposed in serial array, a pasteurizer for cooling work containers comprising:

an adsorption freezing machine between a high temperature cooling vessel disposed at carried-in side of work containers and a low temperature cooling vessel disposed at downstream side; and a cooling tower disposed between the high temperature side cooling vessel at the relatively upstream side position along the cooling direction of the work containers and the cooling vessel at the downstream side thereof, such cooling vessels being within a group of intermediate cooling vessels disposed among cooling vessels connected through the adsorption freezing machine.

4. A pasteurizer for cooling work containers according to claim 3 wherein a cold heat energy of the downstream side cooling vessel in a group of the cooling vessels is supplied to the primary side of a heat exchanger so as to make capable of supplying a cold heat from the secondary side thereof as a cold heat energy spraying liquid to the adjacent upstream side cooling vessel while circulating to the storage tray of the same temperature as the primary side stored liquid which is heated by giving cold heat.

5. In a pasteurizer which sterilizes a liquid filled in work containers with heat energy having a preheating region, heating region, sterilizing region, precooling region and cooling region, which form heat-exchanging function by circulating-spraying between storage trays and spraying parts spraying liquid to work containers such as cans, bins and so forth along a transporting path from the upstream to the downstream, a pasteurizer for sterilization comprising:

a line for supplying a cold heat or heat energy which forms and holds each temperature region in the each storage tray;

a cross-linked circulating path for spraying liquid which is formed between a circulating spray liquid of the preheating region sprayed in the precooling region and a circulating spray liquid of the precooling region sprayed in the preheating region;

a line for supplying a low temperature which makes a low temperature circulating spray by supplying a cold heat energy to a heat-exchanging chamber of the cooling region; and a line for replenishing a stored liquid replenishing a stored liquid to an upstream side storage tray by cooling and storing overflow liquid of each storage tray.

6. A pasteurizer for sterilization according to claim 5 wherein a ratio of heat treating time of preheating, heating, sterilizing, precooling and cooling is 1:1:2:1:1.

7. A pasteurizer for sterilization according to claim 5 wherein water is used as a spraying liquid and a storage liquid in a line for supplying a cold heat or heat energy and a water supplying line is used for supplying cold heat energy and a steam supplying line is used for supplying heat energy.

8. A pasteurizer for sterilization according to claim 5 wherein cold heat is supplied from a cooling part which supplies cold heat energy to the line for supplying a low temperature and the line for replenishing the stored liquid through the cooling tower.

* * * * *